US010159444B2

(12) United States Patent
Lin et al.

(10) Patent No.: US 10,159,444 B2
(45) Date of Patent: Dec. 25, 2018

(54) METHOD AND SYSTEM FOR ANAEROBIC THRESHOLD HEART RATE DETECTION

(71) Applicant: INDUSTRIAL TECHNOLOGY RESEARCH INSTITUTE, Hsinchu Hsien (TW)

(72) Inventors: Hsing-Chen Lin, Hsinchu (TW); Jong-Shyan Wang, Hsinchu (TW); Chi-Hsiang Weng, Hsinchu (TW); Ching-Yu Huang, Hsinchu (TW); Wen-Chung Hsueh, Hsinchu (TW)

(73) Assignee: INDUSTRIAL TECHNOLOGY RESEARCH INSTITUTE, Hsinchu Hsien (TW)

( * ) Notice: Subject to any disclaimer, the term of this patent is extended or adjusted under 35 U.S.C. 154(b) by 320 days.

(21) Appl. No.: 14/976,831

(22) Filed: Dec. 21, 2015

(65) Prior Publication Data

US 2017/0172513 A1 Jun. 22, 2017

(51) Int. Cl.
*A61B 5/00* (2006.01)
*A61B 5/0245* (2006.01)
*A61B 5/0456* (2006.01)

(52) U.S. Cl.
CPC .......... *A61B 5/7246* (2013.01); *A61B 5/0245* (2013.01); *A61B 5/0456* (2013.01); *A61B 5/681* (2013.01); *A61B 5/6802* (2013.01); *A61B 5/6898* (2013.01); *A61B 5/7235* (2013.01); *A61B 5/7282* (2013.01); *A61B 2503/10* (2013.01)

(58) Field of Classification Search
CPC ... A61B 5/7235; A61B 5/7239; A61B 5/7246; A61B 5/4866; A61B 5/0205
See application file for complete search history.

(56) References Cited

U.S. PATENT DOCUMENTS

| | | | |
|---|---|---|---|
| 5,782,772 | A | 7/1998 | Stegmann |
| 8,911,329 | B2 | 12/2014 | Lin et al. |
| 9,855,007 | B2 * | 1/2018 | Jouanique-Dubuis ....................... A61B 5/7225 |
| 2011/0040193 | A1 | 2/2011 | Seppanen et al. |

FOREIGN PATENT DOCUMENTS

| | | |
|---|---|---|
| CN | 1968293 | 5/2007 |
| CN | 103815911 | 5/2014 |
| TW | 555544 | 10/2003 |
| TW | I321465 | 3/2010 |
| TW | 201500032 | 1/2015 |
| TW | 201537375 | 10/2015 |
| TW | 200537901 | 11/2015 |

OTHER PUBLICATIONS

Taiwanese Office Action for Taiwanese Patent Application No. 104142921 dated Jun. 16, 2016.

* cited by examiner

*Primary Examiner* — Michael Kahelin
(74) *Attorney, Agent, or Firm* — Amin, Turocy & Watson LLP

(57) ABSTRACT

The disclosure provides a method and system for detecting an anaerobic threshold heart rate. After first physiological data, second physiological data and third physiological data are obtained while a user is exercising, an interval of the third physiological data corresponding to an estimated range of first physiological data and a turning point of a curve fitting the third physiological data within the interval are obtained, to determine the anaerobic threshold heart rate of a user.

9 Claims, 4 Drawing Sheets

200
160
150
140
100
50
0 20 40 60 80 100 120
$HR_{AT}$ = 153 bpm
heart rate
411
412
413
414
60
40
20
0
SDNN
421
422
423
5
0
-5
curvature of SDNN
431
432
433
434

METHOD AND SYSTEM FOR ANAEROBIC THRESHOLD HEART RATE DETECTION

TECHNICAL FIELD

The disclosure relates to a method and system for detecting heat rates, and relates to a method and system for detecting an anaerobic threshold heart rate.

BACKGROUND

Generally, exercises can be grouped into aerobic exercises, and anaerobic exercises. An aerobic exercise is performed at a low to moderate level of intensity over a long period of time, and an anaerobic exercise is performed at a high level of intensity. Under a long duration of an anaerobic exercise, an exerciser may accumulate excessive lactate, which causes muscular fatigue.

To identify whether an exercise is aerobic or anaerobic, an anaerobic threshold (AT) is needed. The anaerobic threshold is the point at which the exercise changes from aerobic to anaerobic. The anaerobic threshold (also called the lactate threshold) is defined as the level of exercise intensity at which lactate produces faster than it can be metabolized, and the heart rate at this point is called the anaerobic threshold heart rate.

The anaerobic threshold heart rate varies depending on an individual's physical conditions. The anaerobic threshold heart rate is generally estimated through measurement of ventilation rate or blood lactate. However, such a measurement is implemented by bulky and expensive instruments or blood sampling and testing processes need to be performed many times, thus bringing much inconvenience.

SUMMARY

In an embodiment, the method for detecting an anaerobic threshold heart rate comprises: obtaining first physiological data, second physiological data and third physiological data while the user is exercising, wherein the third physiological data may be calculated based on the second physiological data; obtaining an interval of the third physiological data corresponding to an estimated range of the first physiological data; and obtaining a turning point of a curve fitting the third physiological data within the interval to determine the anaerobic threshold heart rate of the user.

In an embodiment, the system for detecting an anaerobic threshold heart rate of a user comprises: a monitoring unit configured to obtain the first physiological data and the second physiological data while the user is exercising; and a microprocessor configured to receive the first physiological data and the second physiological data from the monitoring unit. In an embodiment, the microprocessor comprises: a first calculating module configured to calculate the third physiological data based on the second physiological data; and a second calculating module configured to obtain an interval of the third physiological data corresponding to an estimated range of the first physiological data, and obtain a turning point of a curve fitting the third physiological data within the interval to determine the anaerobic threshold heart rate of the user.

DETAILED DESCRIPTION

Figure 1:
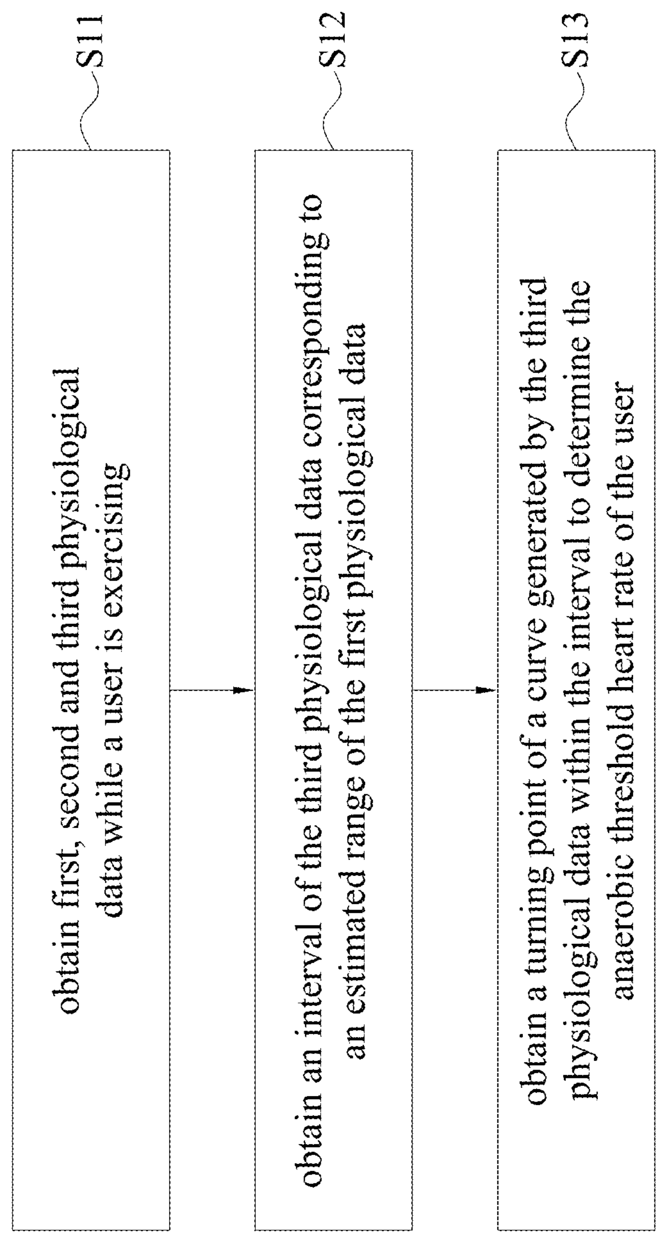
FIG. 1 is a flow chart illustrating a method for detecting an anaerobic threshold heart rate of a user according to the disclosure.

In the following detailed descriptions, for purposes of explanation, numerous details are set forth in order to provide a thorough understanding of the disclosed embodiments. It will be apparent, however, that one or more embodiments may be practiced without these details. In other instances, well-known structures and devices are schematically shown in order to simplify the drawing.

The disclosure provides a convenient method and system for detecting an anaerobic threshold heart rate of a user so as to dispense with the bulk and expensive instruments or a plurality of blood samplings and testing processes. The disclosure also facilitates planning of a personalized physical fitness exercise program.

The method and system for detecting an anaerobic threshold heart rate of a user according to the disclosure are convenient and have low complexity of computation. An interval of the third physiological data may be obtained according to an estimated range of the first physiological data, and a turning point of a curve fitting the third physiological data within the interval may be obtained to determine the anaerobic threshold heart rate of the user, thereby facilitating the user to plan a personalized physical fitness exercise program.

FIG. 1 is a flow chart illustrating a method for detecting the anaerobic threshold heart rate of a user according to the disclosure. In step S11, the first physiological data, the second physiological data and the third physiological data are obtained while the user is exercising. The first physiological data may be heart rate data (HR). The second physiological data may be R-R interval (RRI) data which is measured by an electrocardiogram (or a heart rate monitor), or a peak-to-peak interval (PPI) data which is measured by other heart rate measurement devices. The third physiological data may be a standard deviation of normal-to-normal (SDNN) data calculated based on the second physiological data.

The SDNN may be calculated by the equation:

$$SDNN = \sqrt{\frac{1}{N}\sum_{i=1}^{N}(RRI_i - \overline{RRI})^2} \quad \text{or}$$

$$SDNN = \sqrt{\frac{1}{N}\sum_{i=1}^{N}(PPI_i - \overline{PPI})^2},$$

depending on the type of the monitoring unit. Then, the method proceeds to step S12.

In step S12, an interval of the third physiological data corresponding to an estimated range of the first physiological data may be obtained. The so-called estimated range of the first physiological data may be obtained by multiplying a confidence interval that is found from a statistical distribution of estimated maximum heart rates for adults corresponding to the age of the user by a percentage. For example, if the user is 25 years old, the data corresponding to the age of 25 may be obtained from a statistical distribution of estimated maximum heart rates for adults. In an embodiment, a 95% confidence interval may be obtained from the statistical distribution, which may be between 178 and 200 bpm for the age of 25. In an embodiment, the confidence interval may be at, but not limited to, a 95% confidence level. Finally, the confidence interval may be multiplied by a percentage to obtain the estimated range of the first physiological data, and the data of an interval may be obtained by corresponding the estimated range of the first physiological data to the third physiological data. In an embodiment, the percentage may be, but not limited to, 80%. The method goes to step S13.

In step S13, a turning point of the curve fitting the third physiological data within the interval may be obtained to determine the anaerobic threshold heart rate of the user. In an embodiment, a turning point of the curve fitting the third physiological data within the interval may be obtained by calculating the curvature or slope of the SDNN data within the interval, so as to obtain the curve fitting the curvature or slope of the SDNN data, and the position of the turning point is obtained from the curve. The curvature of the SDNN data may be calculated by the following equation:

$$\kappa_{SDNN}=\left[\frac{d^2SDNN(t)}{dt^2}\right]\Big/\left[\left[1+\left(\frac{dSDNN(t)}{dt}\right)^2\right]^{\frac{3}{2}}\right],$$

wherein $\kappa_{SDNN}$ represents the curvature of SDNN, and SDNN(t) represents the function of SDNN at time t.

After the curvature of the third physiological data within the interval is calculated, the anaerobic threshold heart rate of the user can be determined according to the curvature. In an embodiment, the peak of the curve may be taken as the turning point, and the anaerobic threshold heart rate may be the first physiological data at the turning point. In another embodiment, the turning point lies in a position where the third physiological data within the interval is less than a threshold, and the anaerobic threshold heart rate of the user may be the first physiological data at the turning point. For example, the threshold may be, but not limited to, 20 (SDNN). In an embodiment, the turning point lies in a position where the curve of the third physiological data within the interval goes down gradually with time and tends to become flat, and the anaerobic threshold heart rate of the user may be the first physiological data at the turning point. The so-called "a position where the curve . . . goes down gradually with time and tends to become flat" refers to a position where the slope of the curve is less than a slope threshold and kept for a time duration. The slope threshold and the time duration can be set and slightly adjusted according to different situations. Further, the slope threshold and the time duration are not limited to values. The turning point can lie in any position so long as the curve of the third physiological data within the interval goes down gradually with time and tends to become flat. The above mentioned three methods can be used separately or in a combination. For example, the anaerobic threshold heart rate of the user may be determined by using one of the methods, a combination of two of the methods or a combination of all the three methods.

Figure 2:
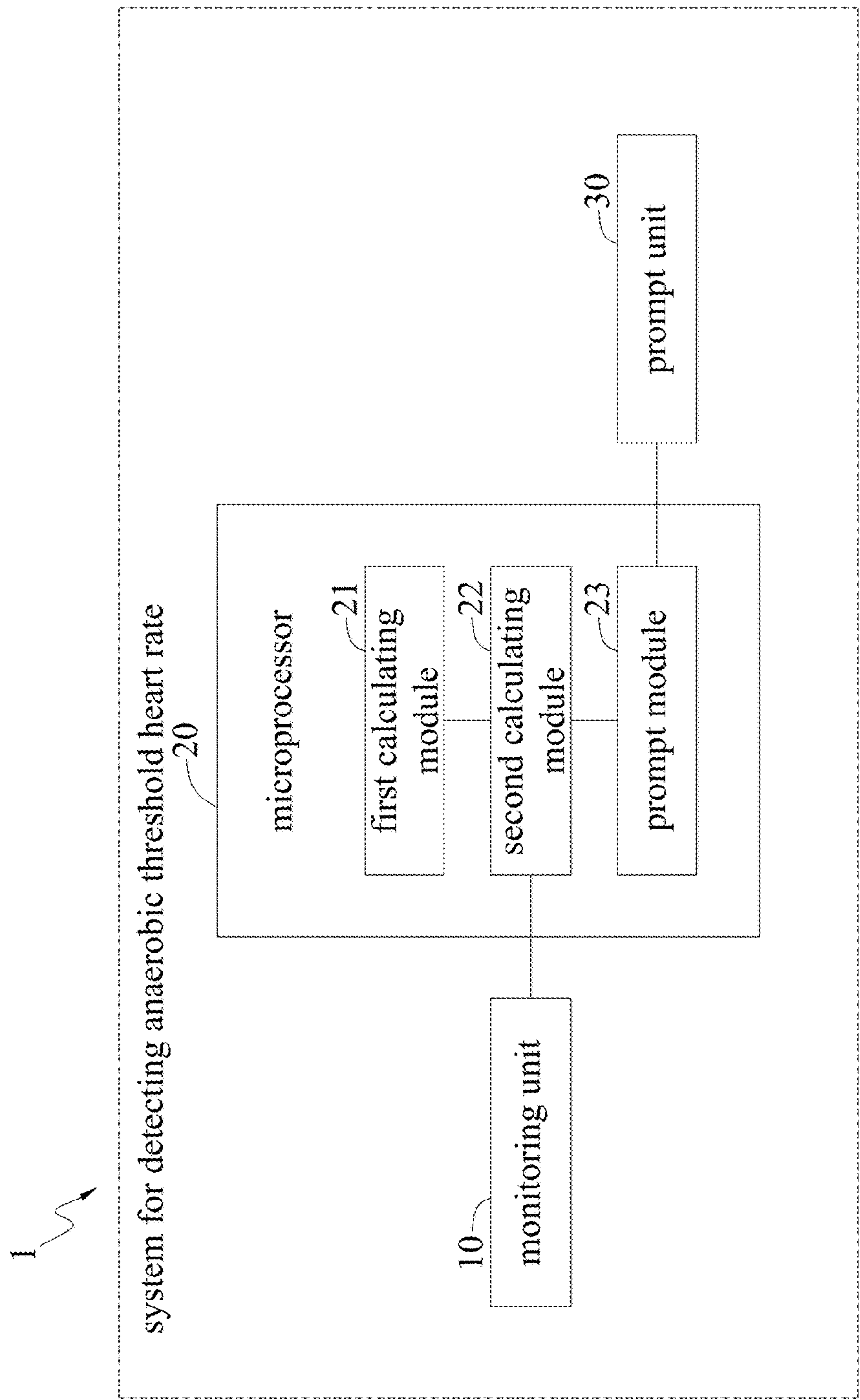
FIG. 2 is a schematic block diagram showing a system for detecting an anaerobic threshold heart rate of a user according to the disclosure.

FIG. 2 is a schematic block diagram showing a system 1 for detecting an anaerobic threshold heart rate of a user according to the disclosure. The system 1 has a monitoring unit 10, a microprocessor 20 and a prompt unit 30. In an embodiment, the microprocessor 20 may be embedded with a plurality of calculating modules, including a first calculating module 21, a second calculating module 22 and a prompt module 23. The modules refer to software or firmware executed by the microprocessor 20.

The monitoring unit 10 may be used to obtain the first physiological data and the second physiological data while the user is exercising. In an embodiment, the monitoring unit 10 may be a heart rate sensor, the first physiological data may be heart rate data, and the second physiological data may be R-R interval (RRI) data or peak-to-peak interval (PPI) data.

After receiving the first physiological data and the second physiological data from the monitoring unit 10, the microprocessor 20 controls the first calculating module 21 to calculate a third physiological data based on the second physiological data. The third physiological data may be the standard deviation of normal-to-normal (SDNN) data, and can be calculated as described previously, further description hereby omitted.

The second calculating module 22 obtains an interval of the third physiological data corresponding to an estimated range of the first physiological data, obtains a curve fitting the third physiological data within the interval, and obtains a position of a turning point from the curve, so as to determine the anaerobic threshold heart rate of the user. In an embodiment, the second calculating module 22 obtains the age of the user, gives a confidence interval of a statistical distribution of estimated maximum heart rates for adults corresponding to the age of the user, and multiplies the confidence interval by a percentage to obtain the estimated range of the first physiological data. Then, an interval of the third physiological data corresponding to the estimated range of the first physiological data may be obtained, and curvature or slope of the curve of the third physiological data within the interval may be calculated. Finally, a peak of the curvature of the curve may be taken as a turning point, and the anaerobic threshold heart rate of the user may be the first physiological data at the turning point. In an embodiment, in addition to determining the anaerobic threshold heart rate according to the peak of the curvature of the third physiological data within the interval, a position where the third physiological data within the interval is less than a threshold may be taken as the turning point, or a position where the curve of the third physiological data within the interval goes down gradually and becomes flat may be taken as the turning point, and the anaerobic threshold heart rate of the user may be the first physiological data at the turning point. The present disclosure is not limited thereto. The calculation described therein has been described previously, further description hereby omitted.

Figure 3:
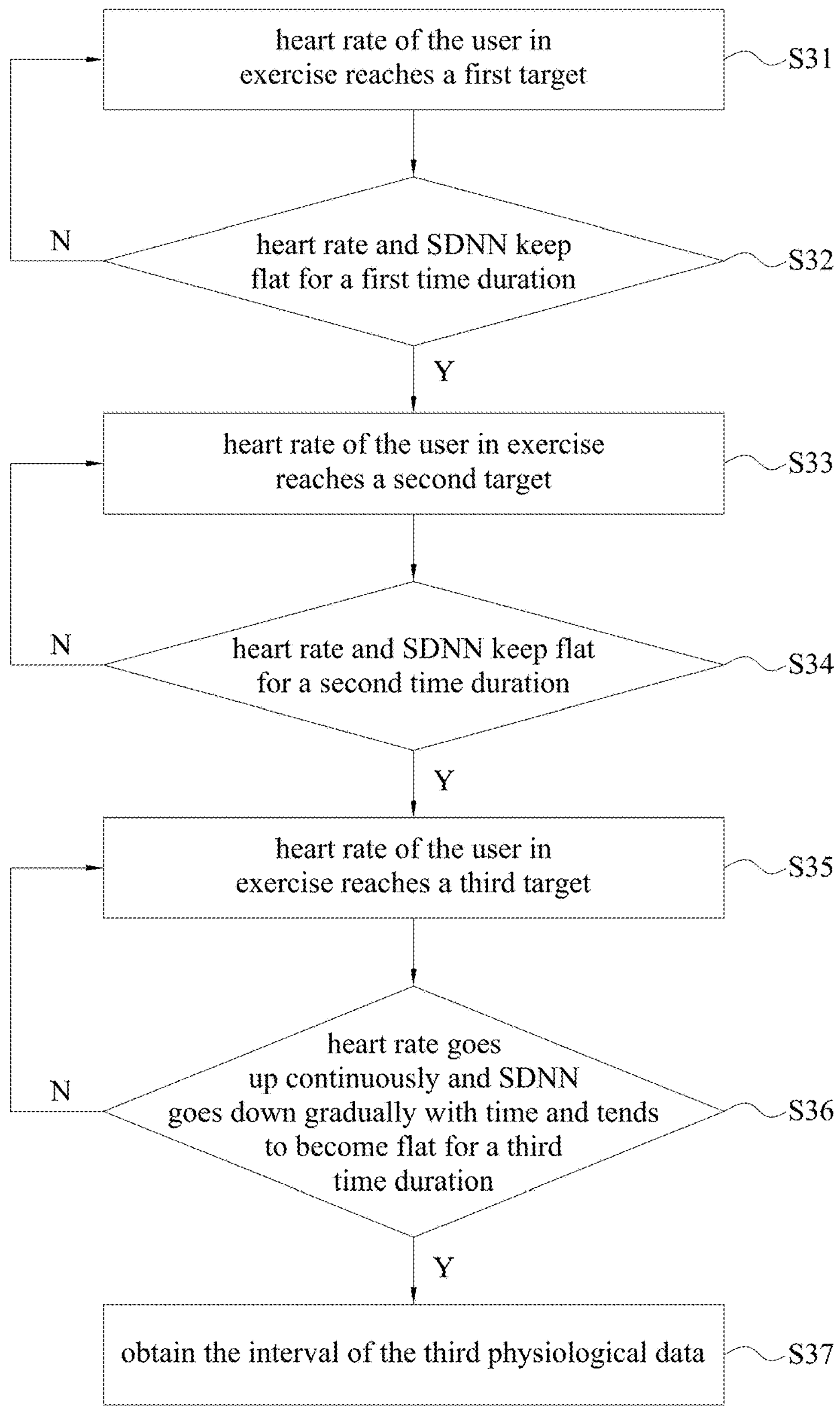
FIG. 3 is a schematic flow chart showing an exercise prompt process according to an embodiment of the disclosure.

The prompt module 23 may be used to guide the user to find a personal anaerobic threshold heart rate, as designed as an exercise prompt (or an exercise guide) shown in FIG. 3, which guide the user to obtain SDNN data having an clearer turning point within the interval, thereby facilitating automatic determination of the personal anaerobic threshold heart rate. In an embodiment, the prompt module 23 controls operation of the prompt unit 30 according to the first physiological data or the anaerobic threshold heart rate of the user while the user is exercising. In an embodiment, the prompt unit 30 may be a speaker or light source. When the heart rate and SDNN reach a target and keep flat for a time duration, the prompt module 23 can control the prompt unit 30 to operate so as to prompt the user to increase the exercise intensity.

The flow chart of FIG. 3 is detailed as follows. In step S31, the heart rate of the user in exercise reaches a first target. The first target may be set according to the equation:

$$z = \text{an estimated maximum heart rate for adults} \times y,$$

wherein z represents a heart rate, and y may be in a range varied from 20% to 80%. The estimated maximum heart rate for adults can be calculated in several ways, but not limited to. In an embodiment, $z=(220-x)\times y$, wherein x is the age of the user.

For example, if the user is 25 years old, the first target may be set to be $(220-25)\times 60\%$. The heart rate and SDNN of the user are kept flat for a first time duration in step S32. If the user can maintain the heart rate and SDNN, the method proceeds to step S33; otherwise, the user increases the exercise intensity.

Similarly, in steps S33 and S34, the heart rate of the user in exercise reaches a second target, and the heart rate and SDNN are kept flat for a second time duration. The second target may be greater than the first target. For example, the first target may be $(220-25)\times 60\%$, and the second target may be $(220-25)\times 70\%$. If the user can maintain the heart rate and SDNN, the method proceeds to step S35; otherwise, the user increases the exercise intensity.

Similarly, in steps S35 and S36, the heart rate of the user in exercise reaches a third target, the heart rate goes up continuously, and the SDNN goes down gradually with time and tends to become flat for a third time duration. If the requirement is met, the method proceeds to step S37; otherwise, the method proceeds to step S35. The third target may be greater than the first target and the second target. In an embodiment, the first target may be $(220-25)\times 60\%$, the second target may be $(220-25)\times 70\%$, and the third target may be $(220-25)\times 80\%$.

At least one or more targets can be set, and the final target may be set to be $(220-25)\times 80\%$. Alternatively, the estimated range of the first physiological data or other parameters according to the physical conditions of the user can be set as the target, and the disclosure is not limited thereto. In step S37, the interval of the third physiological data may be obtained.

Therefore, after step S32, S34 or S36 of FIG. 3, the prompt module 23 controls the prompt unit 30 to prompt the user to go to the next detection step; or after step S13 of FIG. 1 or step S37 of FIG. 3, the prompt module 23 controls the prompt unit 30 to inform the user that the process is ended.

Figure 4:
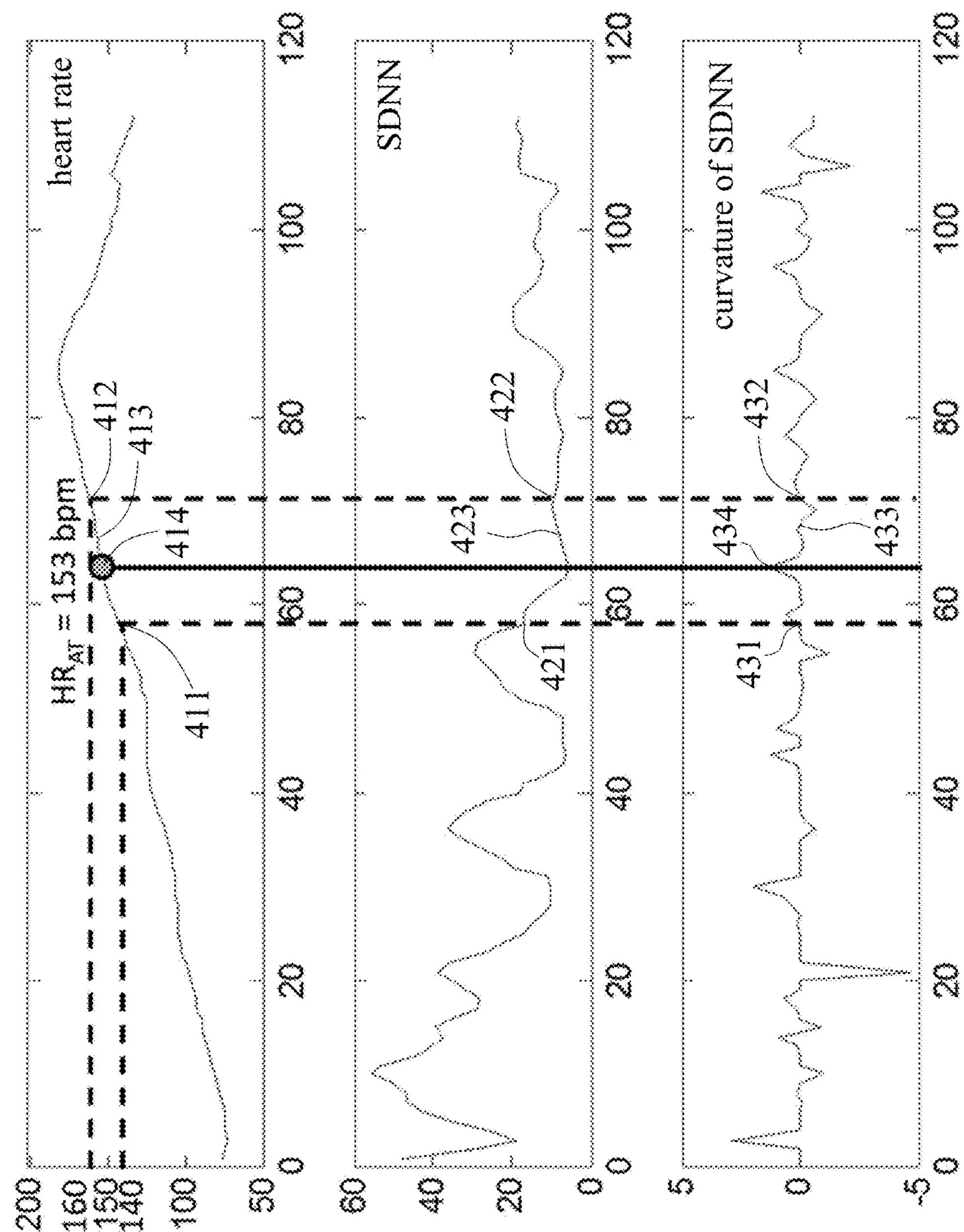
FIG. 4 illustrates graphs showing relationships between heart rate, standard deviation of normal-to-normal (SDNN) and curvature of SDNN according to the disclosure.

FIG. 4 shows relationships between the heart rate, the SDNN and the curvature of the SDNN according to the disclosure. In an embodiment, if the user is 25 years old, the obtained estimated range of the first physiological data may be a segment 413 of the curve of heart rate between points 411, 412, which corresponds to a heart rate of 140 to 160 bpm. Then, the points 411, 412 and the segment 413 are corresponded to the curve of SDNN so as to obtain data of points 421, 422 and a segment 423. Thereafter, the curvature of SDNN may be calculated according to the SDNN data of the points 421, 422 and the segment 423 so as to form a curve of the curvature of the SDNN and to obtain the curvature of the SDNN data of points 431, 432 and a segment 433. A peak, i.e., a point 434 may be found from the curve of the curvature of the SDNN, and the position of the point 434 can be corresponded back to a point 414 of the curve of the heart rate. The point 414 may be the anaerobic threshold heart rate of the user, which is, for example, 153 bpm. The description of this corresponding way is an exemplary embodiment according to the disclosure, and the disclosure is not limited thereto.

In an embodiment, the system 1 can be embedded on a wearable device, such as a smart watch, a bracelet or a mobile phone. Alternatively, the system 1 may be an app software.

According to the disclosure, SDNN may be calculated according to heart rates of a user, and the anaerobic threshold heart rate of the user may be obtained from an interval of the SDNN so as to facilitate the user to plan a personalized physical fitness exercise program. The disclosure is convenient and has low complexity of calculation.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A system for detecting an anaerobic threshold heart rate of a user, comprising:

- a heart rate sensor configured to obtain first physiological data and second physiological data while the user is exercising; and
- a microprocessor configured to receive the first physiological data and the second physiological data from the heart rate sensor and configured to implement a first calculating module and a second calculating module:
  - the first calculating module configured to calculate third physiological data according to the second physiological data; and
  - the second calculating module configured to obtain an interval of the third physiological data corresponding to an estimated range of the first physiological data, and obtain a turning point of a curve fitting the third physiological data within the interval to determine the anaerobic threshold heart rate of the user,
- wherein the first physiological data is heart rate data, the second physiological data is R-R interval data or peak-to-peak interval data, and the third physiological data is standard deviation of normal-to-normal data.

2. The system of claim 1, wherein the second calculating module is configured to obtain the estimated range of the first physiological data by multiplying a confidence interval of a statistical distribution of estimated maximum heart rates for adults corresponding to the age of the user by a percentage.

3. The system of claim 1, wherein the second calculating module is configured to determine the turning point by a curvature or slope of the curve.

4. The system of claim 3, wherein the second calculating module is configured to lie the turning point at a peak of the curvature of the curve, and the second calculating module is configured to determine the anaerobic threshold heart rate of the user by the first physiological data corresponding to the turning point.

5. The system of claim 1, wherein the second calculating module is configured to lie the turning point in a position where the third physiological data within the interval is less than a threshold, and the second calculating module is configured to determine the anaerobic threshold heart rate of the user by the first physiological data corresponding to the turning point.

6. The system of claim 1, wherein the second calculating module is configured to lie the turning point in a position where the curve of the third physiological data within the interval goes down gradually with time and tends to become flat, and the second calculating module is configured to determine the anaerobic threshold heart rate of the user by the first physiological data corresponding to the turning point.

7. The system of claim 1, wherein the second calculating module is configured to obtain the first physiological data and the second physiological data as the first physiological data of the user reached at least a target and the first physiological data and the third physiological data kept flat for a time duration.

8. The system of claim 7, wherein the second calculating module is configured to calculate the target by the following equation:

$$z = \text{an estimated maximum heart rate for adults} \times y,$$

wherein z represents a heart rate, and y is in a range varied from 20% to 80%.

9. The system of claim 1, wherein the microprocessor further comprises a prompt module configured to control a prompt device according to the first physiological data or the anaerobic threshold heart rate of the user.

* * * * *